(12) United States Patent
Rabin et al.

(10) Patent No.: US 12,402,888 B2
(45) Date of Patent: Sep. 2, 2025

(54) TRANS-ESOPHAGEAL AORTIC FLOW RATE CONTROL

(71) Applicant: University of Maryland, Baltimore, Baltimore, MD (US)

(72) Inventors: Joseph Rabin, Silver Spring, MD (US); Zhongjun Wu, Marriottsville, MD (US)

(73) Assignee: University of Maryland, Baltimore, Baltimore, MD (US)

(*) Notice: Subject to any disclaimer, the term of this patent is extended or adjusted under 35 U.S.C. 154(b) by 30 days.

(21) Appl. No.: 18/064,989

(22) Filed: Dec. 13, 2022

(65) Prior Publication Data

US 2023/0225741 A1 Jul. 20, 2023

Related U.S. Application Data

(63) Continuation of application No. 16/978,280, filed as application No. PCT/US2019/020693 on Mar. 5, 2019, now Pat. No. 11,523,832.

(60) Provisional application No. 62/638,600, filed on Mar. 5, 2018.

(51) Int. Cl.
*A61B 17/128* (2006.01)
*A61B 17/12* (2006.01)
*A61B 17/29* (2006.01)
*A61B 17/00* (2006.01)

(52) U.S. Cl.
CPC .... *A61B 17/1285* (2013.01); *A61B 17/12022* (2013.01); *A61B 17/29* (2013.01); *A61B 2017/00278* (2013.01); *A61B 2017/1205* (2013.01); *A61B 2017/2905* (2013.01); *A61B 2017/2947* (2013.01)

(58) Field of Classification Search
CPC .......... A61B 17/1285; A61B 17/12022; A61B 17/29; A61B 2017/00278; A61B 2017/1205; A61B 2017/2905; A61B 2017/2947
See application file for complete search history.

(56) References Cited

U.S. PATENT DOCUMENTS

2007/0239170 A1* 10/2007 Brock ................ A61B 17/0483
606/1
2013/0197555 A1* 8/2013 Schaer ................ A61N 7/022
606/170

* cited by examiner

*Primary Examiner* — Brooke Labranche
(74) *Attorney, Agent, or Firm* — Whiteford, Taylor & Preston, LLP; Gregory M. Stone

(57) ABSTRACT

A device and method is provided herein for esophageal impingement of a patient's aorta. The device may be inserted into a patient's esophagus and positioned at the location where the esophagus passes over the patient's aorta. In this position, an actuation device is used to apply pressure to the patient's aorta through their esophagus to impinge or occlude the aorta to stop or significantly reduce hemorrhaging. A manually operable actuator handle enables a physician to manipulate a head assembly of the device through three distinct degrees of freedom of movement so as to control placement and direction of force against the patient's esophagus and, in turn, their aorta.

15 Claims, 14 Drawing Sheets

TRANS-ESOPHAGEAL AORTIC FLOW RATE CONTROL

CROSS REFERENCE TO RELATED APPLICATION

This application is a continuation of U.S. patent application Ser. No. 16/978,280 entitled "TRANS-ESOPHAGEAL AORTIC FLOW RATE CONTROL," filed with the United States Patent and Trademark Office on Sep. 4, 2020, now U.S. Pat. No. 11,523,832, which is a national stage entry of International Patent Application No. PCT/US2019/020693, titled "TRANS-ESOPHAGEAL AORTIC FLOW RATE CONTROL," filed with the United States Patent and Trademark Office on Mar. 5, 2019, which application claims the benefit of U.S. Provisional Application No. 62/638,600 titled "TRANS-ESOPHAGEAL AORTIC FLOW RATE CONTROL," filed Mar. 5, 2018 by the inventors herein, which applications are incorporated herein by reference in their entireties.

FIELD OF THE INVENTION

The present invention relates generally to methods and apparatus for the treatment of hemorrhaging, and more particularly to methods and apparatus for minimally-invasive control of aortic blood pressure to mitigate hemorrhaging, and particularly non-compressible abdominal hemorrhaging.

BACKGROUND

Non-compressible abdominal wound hemorrhage is one of the leading causes of preventable death in both civilian and military trauma. In trauma injuries, most early deaths are caused by hemorrhage, and according to studies occur at a median of 2.6 hours after admission. Additionally, hemorrhage is responsible for 40% of civilian trauma-related deaths, and for more than 90% of military deaths that result from otherwise potentially survivable injuries. According to some professionals, about 67.3% of deaths on the battlefield are the result of hemorrhage from a wound to the truncal area. Although there are many devices developed that stop hemorrhage, many of them are not sufficient to stop internal bleeding in certain areas, such as the abdomen.

There are a number of preexisting devices that attempt to tackle this issue but fall short of fulfilling the desired outcome. These devices are either largely theoretical, such as the chemical expanding foam RESQFOAM (available from Arsenal Medical), which describes a chemical compound that is inserted into the wound site itself and then expands to take up the entire abdominal cavity, thus putting pressure on the damaged tissue. However, the inserted foam is not biodegradable and must be completely surgically removed prior to the surgeon sewing up the wound. This process can easily result in complications and, thus, should be avoided. Still other devices, such as the Abdominal Aortic and Junctional Tourniquet (AAJT), are only capable of preventing blood loss in juncture and not in abdominal wounds. An AAJT places pressure around the wounded area using a large belt-like device that is fastened. While this device has been implemented to a limited extent, the AAJT has only seen real success in stopping junctural hemorrhages and not abdominal hemorrhages. Thus, a device and method are still required to be effective in this area and to be deployed in emergency medicine.

The most successful and prevalent device on the market currently is the REBOA catheter that is capable of consistently preventing blood loss, but can only be implemented in an operating room by a surgeon, and requires time that trauma patients often do not have.

Thus, unlike wounds to the extremities, normal methods of treatment to stop bleeding such as simple compression or tourniquets are ineffective in abdominal wounds. These wounds often involve internal bleeding and organ damage, such that applying pressure does not reach the internal wound. Therefore, there remains a need for improved methods and devices capable of decreasing the number of preventable deaths from abdominal hemorrhage.

SUMMARY OF THE INVENTION

Disclosed herein are relatively non-invasive methods and apparatus that, with respect to certain features of an embodiment of the invention, may resolve at least some of the foregoing problems. The methods and apparatus according to certain aspects of an embodiment are configured to be easily inserted into a patient's esophagus in order to apply posterior pressure to the patient's aorta. The applied pressure from the device results in the impingement or occlusion of the aorta, such that blood flow is significantly reduced if not eliminated in the lower portion of the body, including the abdomen. This allows medical professionals to extend the life of a patient while the wound is repaired. The device and its method of use are sufficiently simple so as to not require that it be administered by a surgeon, and thus can be used by many health professionals.

In certain configurations, methods and devices as disclosed herein are minimally invasive, are configured to prevent flow rather than pressure the wound directly, and are capable of insertion by emergency services in the field.

A device configured in accordance with certain aspects of an embodiment can be used by a wider range of medical personnel than previously known abdominal hemorrhage control devices due to its ease of use and non-invasiveness. This allows for using the device in locations other than operating rooms. There are many patients that could benefit from a device configured in accordance with such aspects of the invention, such as soldiers in the battlefield or patients admitted to hospitals due to injuries related to gunshots or stabbing.

A device according to certain aspects of an embodiment includes an esophageal tube and an actuator. In certain configurations, at least a portion of the actuator may be situated in a sleeve. In certain configurations, the device may include an anchor-like component, such as at least one balloon (e.g., a gastric balloon) to secure placement of the actuator and/or esophageal tube within the patient.

In accordance with certain aspects of an embodiment, the device may use magnets as the actuator to apply a force inside the body. In Magnets in Medicine, the author reviews how magnets have been widely used in medicine, and are safe to use as long as the proper precautions are taken. Before using medical devices with magnets, a medical professional should clear the area of metals that may interact with the magnetic field, and consult the patient about any devices, such as pacemakers, that may have an interaction. Magnets provide a non-contact force that can be used internally in difficult to reach locations, such as the aorta. The force of a magnet decreases with distance away from the magnet, such that the ideal specifications of the magnet are important to consider for each medical application.

In accordance with further aspects of an embodiment, a trans-esophageal aortic flow control device is provided that includes a mechanical actuator positioned at the distal end of an elongate tube. A handle is positioned at the proximal end of the tube, and is operatively attached to the mechanical actuator such that manipulation of portions of the handle control movement of the mechanical actuator to, in turn, apply pressure to the interior wall of the patient's esophagus, pushing the esophageal wall toward the patient's aorta and ultimately narrowing or closing the patient's aorta so as to reduce or fully block blood flow through the patient's aorta, thus discontinuing or at least controlling a hemorrhage that is located downstream from the location of the mechanical actuator. With regard to certain aspects of an embodiment, the mechanical actuator is capable of three, distinct degrees of freedom of movement that allow improved control over placement and application of force to the patient's esophagus, and in turn to the patient's aorta, to closely control such forces as the physician may deem necessary for a specific patient.

In accordance with certain aspects of an embodiment of the invention, a device for the esophageal compression of a patient's aorta is disclosed, comprising: an elongate tube; an actuator handle at a proximal end of the elongate tube; and a head assembly at a distal end of the elongate tube; wherein the actuator handle engages the head assembly to cause the head assembly to move through three distinct degrees of freedom of movement to apply pressure to a patient's tissue.

In accordance with further aspects of an embodiment of the invention, a device for the esophageal compression of a patient's aorta is disclosed, comprising: an elongate esophageal tube having a longitudinal axis extending from a proximal end of the esophageal tube to a distal end of the esophageal tube; an actuator handle at the proximal end of the esophageal tube; and a head assembly at a distal end of the esophageal tube; wherein the actuator handle engages the head assembly to (i) expand a width of at least a portion of the head assembly; (ii) pivot at least a portion of the head assembly about a first lateral axis that is perpendicular to the longitudinal axis; and (iii) pivot at least a portion of the head assembly about a second lateral axis that is perpendicular to the longitudinal axis and the first lateral axis.

In accordance with still further aspects of an embodiment of the invention, a method for applying impinging pressure to a patient's aorta from the patient's esophagus is provided, comprising the steps of: providing a device comprising an elongate esophageal tube having a longitudinal axis extending from a proximal end of the esophageal tube to a distal end of the esophageal tube, an actuator handle at the proximal end of the esophageal tube, and a head assembly at a distal end of the esophageal tube, wherein the actuator handle engages the head assembly to (i) expand a width of at least a portion of the head assembly; (ii) pivot at least a first portion of the head assembly about a first lateral axis that is perpendicular to the longitudinal axis; and (iii) pivot at least a second portion of the head assembly about a second lateral axis that is perpendicular to the longitudinal axis and the first lateral axis; positioning the device in the patient's esophagus so that the head assembly is positioned adjacent a crossing of the patient's esophagus over the patient's aorta; and using the actuator handle to manipulate the head assembly to apply impinging pressure to the patient's aorta from the patient's esophagus.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized. The present invention is illustrated by way of example, and not by way of limitation, in the figures of the accompanying drawings, in which like reference numerals refer to similar elements, and in which:

DETAILED DESCRIPTION OF THE PREFERRED EMBODIMENTS

Figure 1:
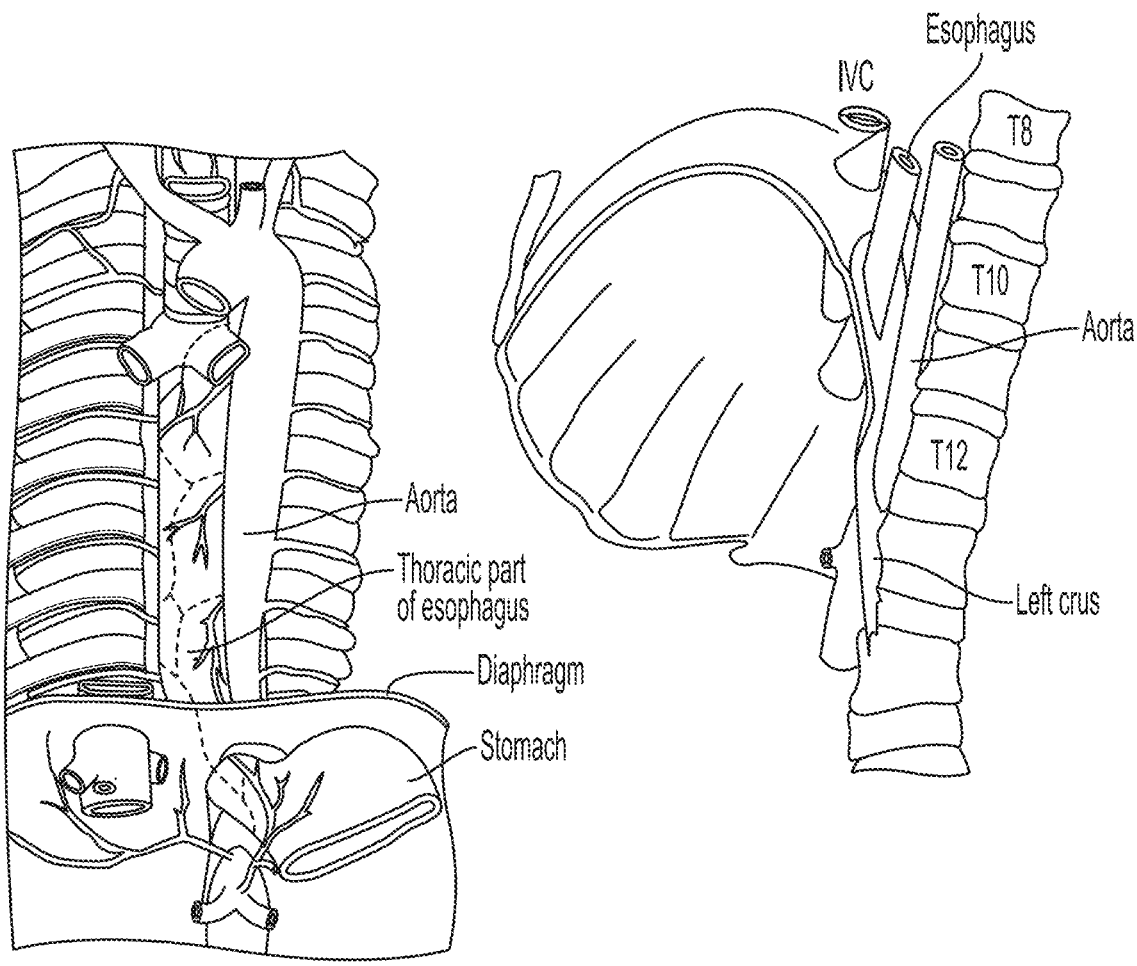
FIG. 1 is an anatomical drawing indicating the typical position of a human esophagus, aorta, and spine.

The following detailed description is provided to gain a comprehensive understanding of the methods, apparatuses and/or systems described herein. Various changes, modifications, and equivalents of the systems, apparatuses and/or methods described herein will suggest themselves to those of ordinary skill in the art.

Descriptions of well-known functions and structures are omitted to enhance clarity and conciseness. The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item.

The use of the terms "first", "second", and the like does not imply any particular order, but they are included to identify individual elements. Moreover, the use of the terms first, second, etc. does not denote any order of importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. Although some features may be described with respect to individual exemplary embodiments, aspects need not be limited thereto such that features from one or more exemplary embodiments may be combinable with other features from one or more exemplary embodiments.

Provided herein are methods and devices that are configured to provide a short-term solution to major hemorrhagic bleeding to prevent extreme blood loss. For example, methods and devices in accordance with certain aspects of an embodiment can be used prior to admission to an emergency facility, while the patient is in the field, and prior to entering an operating room. Thus, the devices and methods disclosed herein are configured to:

Reduce the aortic blood flow rate by up to approximately 90% through applying radial pressure to the aorta to substantially occlude the aorta. This will prevent blood from getting to the wound and, therefore, stop the hemorrhage.

Impinge and/or occlude the aorta by inserting the device into the esophagus to compress the aorta from the patient's esophagus.

The device according to certain aspects of an embodiment includes an esophageal tube and an actuator. At least a portion of the actuator may be positioned within a sleeve. Further, the device may include an anchor, such as at least one balloon (e.g., a gastric balloon) configured to secure placement of the actuator and/or esophageal tube within the patient.

Considering the anatomy of the site of interest, and as shown in FIG. 1 (reproduced from The McGraw-Hill Companies, Inc., copyright 2006), the esophagus and the aorta cross above the intersection with the diaphragm. At this site, the aorta is "sandwiched" between the spine and the esophagus. Thus, a device configured as described herein can be inserted into the esophagus through the mouth to this location, and used to apply posterior pressure against the aorta and toward the patient's spine, which pressure will impinge upon and/or occlude the aorta. The pressure applied to the aorta can be directed towards the posterior side of the body, instead of applying pressure in all directions, to advantageously apply the force on the aorta itself and limit unnecessary stretching of the esophagus. Total aortic occlusion is common practice in many medical procedures that involves clamping the aorta. Clamping the aorta to occlude the aorta may require an external pressure of at least 10 times the internal pressure of the aorta. For example, if an internal aortic pressure is 80 mmHg, an external pressure of 800 mmHg would need to be applied. The required force for this pressure is estimated to be about 15 lbs. However, applying pressure slightly greater than 15 lbs. would not be expected to cause any problems. The device according to certain aspects of an embodiment is preferably less than 4.5 cm in diameter so that it may be easily inserted through the mouth. This diameter is estimated based on other devices that can be inserted through the patient's mouth, however, other diameters that fit into a patient's mouth are feasible.

Figure 3:
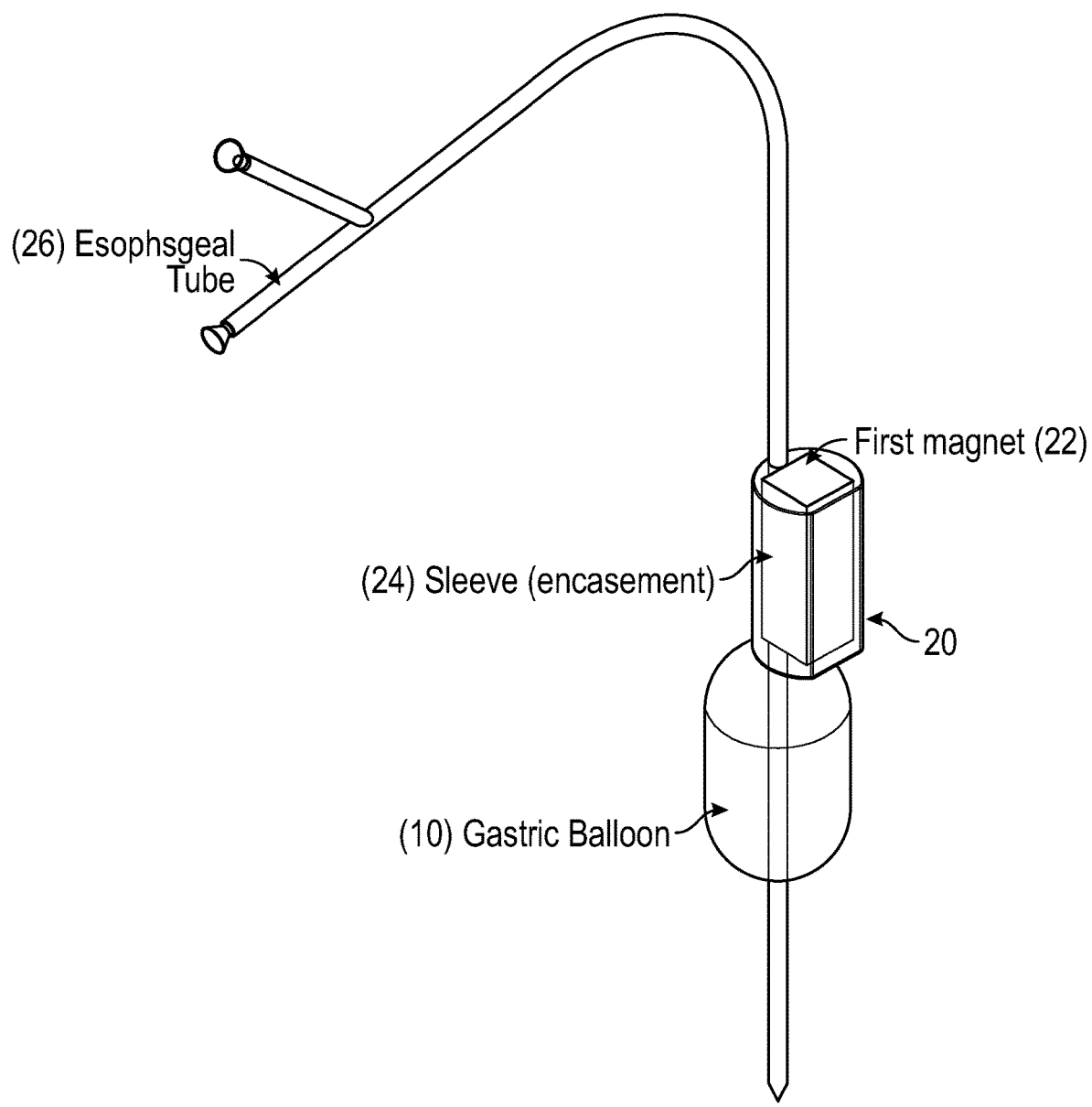
FIG. 3 is a schematic view of a device for occluding a patient's aorta in accordance with certain aspects of an embodiment of the invention.
Figure 4:
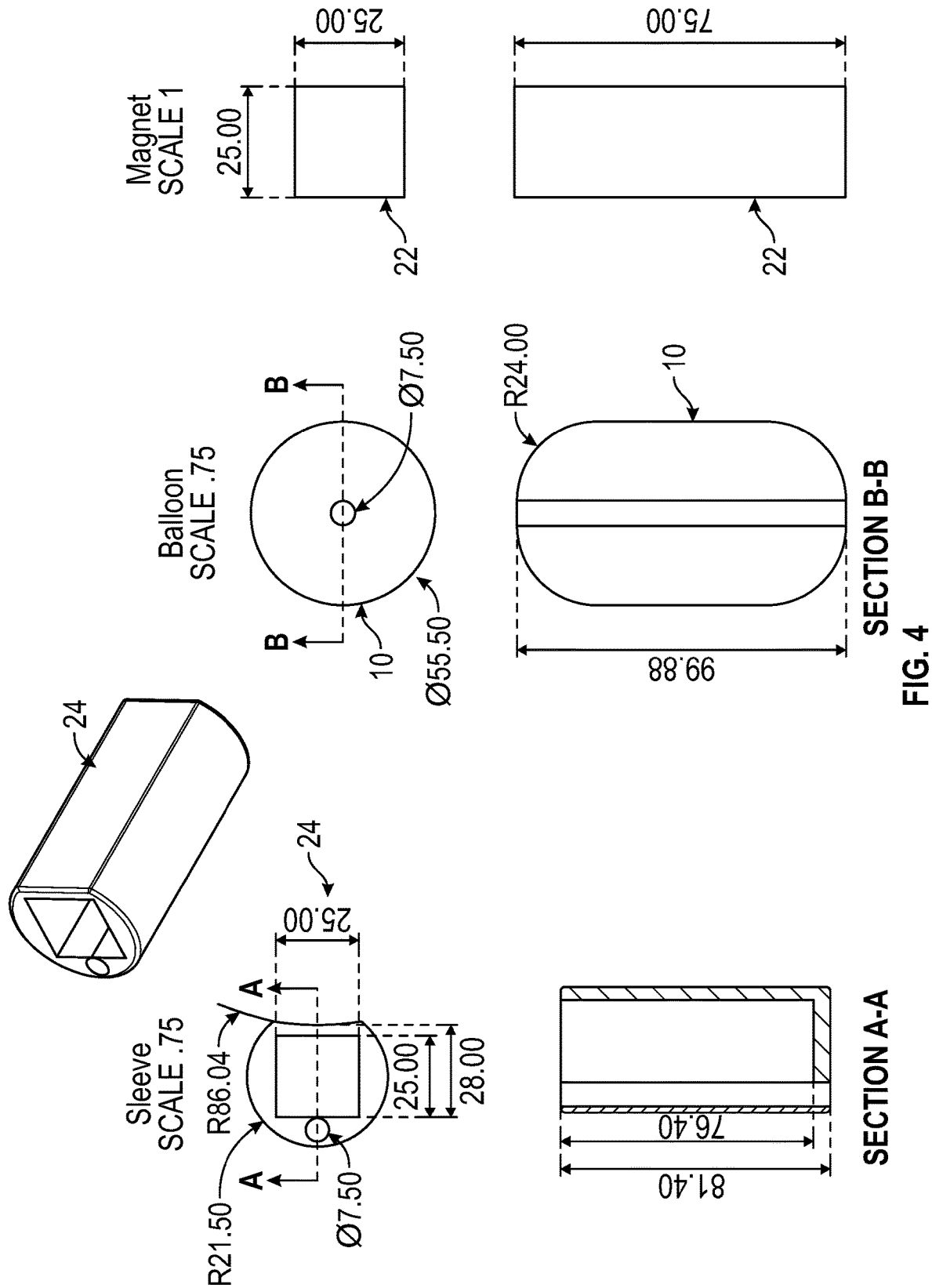
FIG. 4 shows exemplary dimensions of the device for occluding a patient's aorta of FIG. 3.
Figure 5:
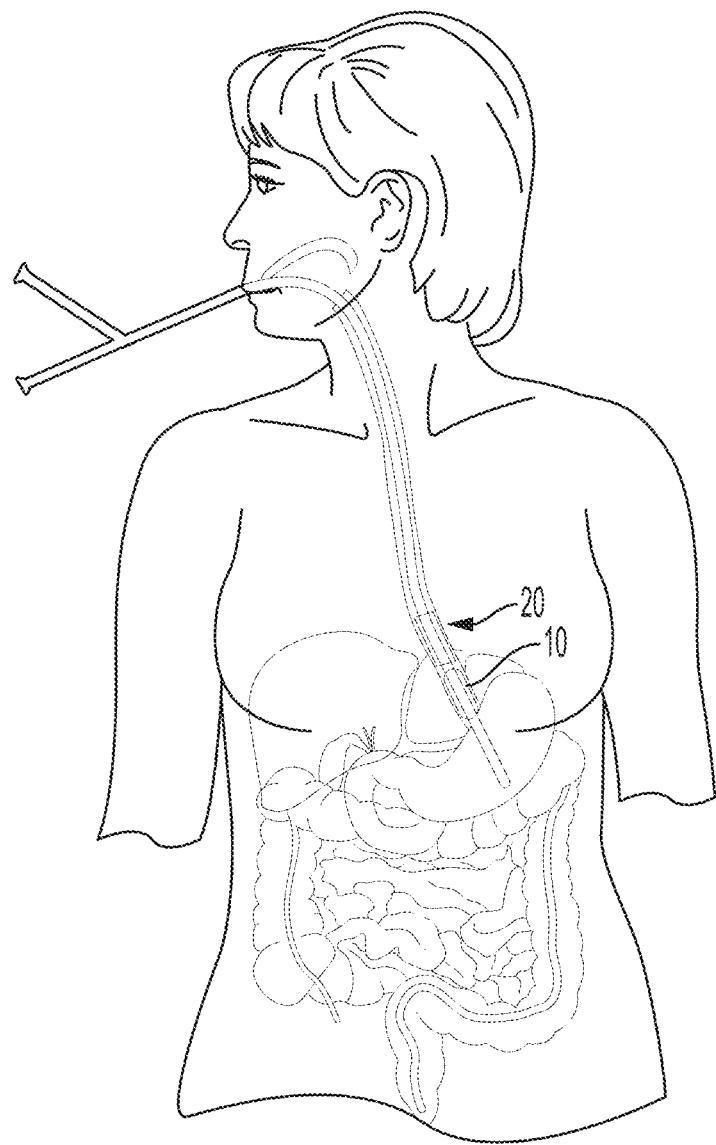
FIG. 5 is a schematic view showing a method for inserting and locating the device of occluding a patient's aorta of FIG. 3 inside of the patient's esophagus.
Figure 6:
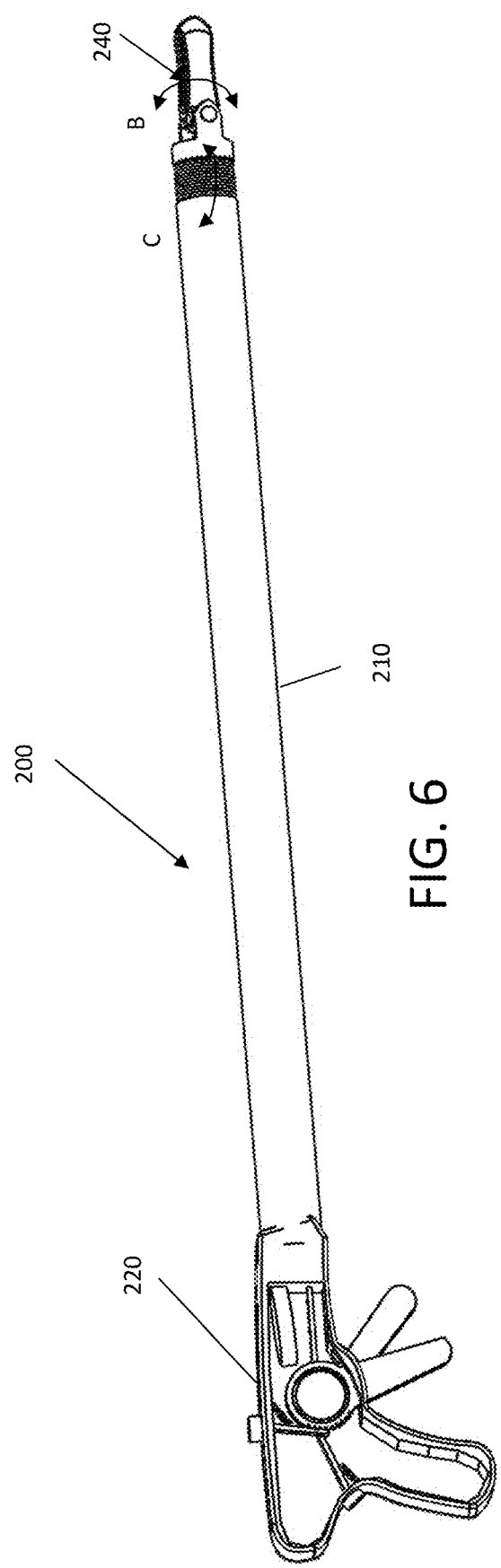
FIG. 6 is a side, partial sectional view of a device for occluding a patient's aorta in accordance with certain aspects of an embodiment of the invention.

As discussed in detail below, a device according to certain aspects of an embodiment includes at least one actuator to apply a force onto a patient's aorta. The actuator is configured to control the direction of the force that is applied to the patient's esophagus, and in turn their aorta. With reference to FIGS. 3-5, the actuator may in one embodiment include one or more magnets. For example, a first magnet may be a small internal magnet and a second magnet may be an external electromagnet. The actuators, such as the magnets, can be positioned to direct forces in a desired direction and with a desired intensity or amplitude (i.e., to control the force).

As discussed in further detail below, the actuator may also comprise other mechanisms that apply an occluding force on the aorta, including pneumatic (e.g., symmetric or asymmetric balloons) or hydraulic forces, and mechanical mechanisms (e.g., caused by a pulley or lever arm, a scissor-like mechanism, rigid or semi-rigid catheter-like mechanisms, stent-like mechanisms, and the like). The magnitude of force can be controlled to further ensure efficiency of the device. There should generally be enough pressure to occlude the aorta, but the pressure should generally be controlled so that it does not damage internal structures such as the aorta, esophagus, and the spine.

Figure 2:
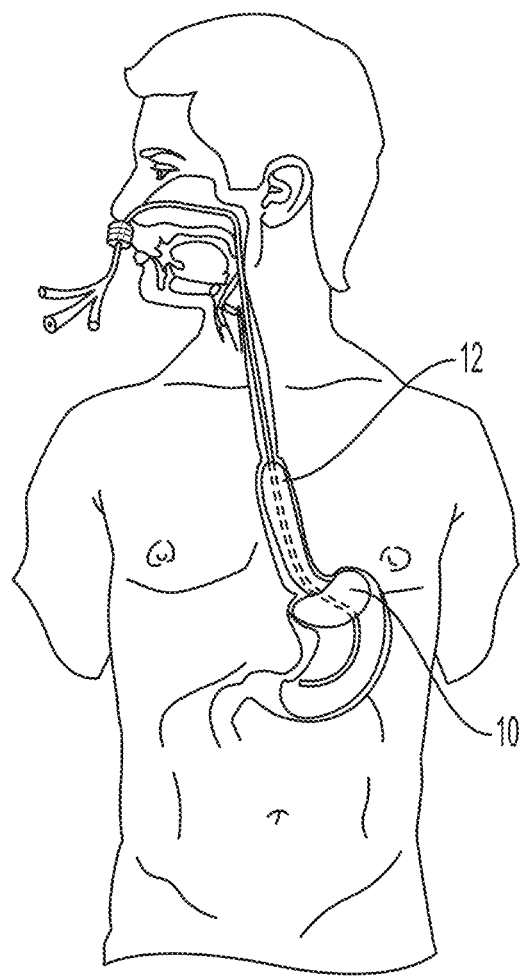
FIG. 2 is a drawing of a gastric balloon that may be used to ensure proper placement of a device as described herein and provide lateral stability.

One embodiment of the device is configured to be more easily inserted and placed at the site of interest than typical devices. For example, and with reference to FIG. 2, a device and method can be used similar to that of the Sengstaken-Blakemore tube. One such embodiment may include a gastric balloon 10 that expands in the stomach to ensure the first balloon 12, or other portions of the device, are in the proper place and not in the stomach. Thus, a device in accordance with certain aspects of an embodiment may include a secondary (stomach or gastric) balloon 10 to ensure that the device is in the desired location and has not gone too far down the patient's esophagus and into the patient's stomach. A device in accordance with certain aspects of an embodiment may also include an esophageal tube for gastric content aspiration to remove the gastric contents from the patient's stomach to reduce the likelihood that the patient will vomit during use of the device.

A device formed in accordance with certain aspects of an embodiment is generally formed of simple materials. As shown in FIG. 3, the device 20 may, in accordance with certain aspects of an embodiment, include two magnets as described above, for example, a first magnet 22 that is positioned in the device (e.g., positioned in the esophageal tube (e.g., from MedEx Supply)) that is relatively smaller and/or weaker than a second magnet. Exemplary magnets may be readily commercially obtained, by way of non-limiting example, from K&J Magnetics, Inc. A device according to certain features of an embodiment may further include a sleeve 24 that can be manufactured according to typical methods, such as by additive manufacturing using CAD drawing designs. The sleeve is configured to be semi-rigid or flexible, such that it is formed of many typical materials, such as Ninjaflex material.

The device according to certain aspects of an embodiment can be assembled by placing the magnet in the sleeve and attaching the sleeve to an esophageal tube 26. In some embodiments, the sleeve 24 can be modified to secure the first magnet 22. Thus, one embodiment of the device includes the first (internal) magnet 22, the sleeve 24, the esophageal tube 26, the second (external) magnet (not shown), and other assembly tools (e.g., sandpaper, scissors, and fasteners or adhesive such as glue). In FIG. 3, an assembled device 20 is shown including an esophageal tube 26, a magnet 22 positioned within an encasement 24, and a gastric balloon 10, and FIG. 4 provides exemplary dimensions for such device.

Testing of a device configured as above can include preliminary testing on an artificial model of the human aorta and esophagus. The artificial model can include a hard plastic spine, flexible plastic aorta, and flexible plastic esophagus. The artificial aorta can be filled with a fluid to mimic the pressure in the aorta. The device can be placed into the artificial esophagus, and the magnets positioned to test the ability of the magnets to occlude the aorta through the esophagus (i.e., induce an occluding force on the aorta by positioning the first and second magnet). FIG. 5 illustrates one embodiment of a method for inserting and locating the device in a patient.

As discussed above, the esophageal tube can be purchased from typical medical device suppliers. In one embodiment of the device, at least one of the first or second magnets is an electromagnet. In another embodiment, the first or second magnet is a large (e.g., 4 in.×4 in.×½ in.) N52 magnet (e.g., as the second or external magnet). In one embodiment, the first (internal) magnet can be a smaller (3 in.×1 in.×1 in.) N52 magnet. In some embodiments, the magnets are encased in plastic to improve the safety of the device.

Next, and in accordance with certain features of a particularly preferred embodiment of the invention, and with reference to FIGS. 6 through 12, a device 200 for esophageal compression of a patient's aorta is provided including an esophageal tube 210, an actuator handle 220 at a proximal end of esophageal tube 210, and a head assembly 240 at a distal end of esophageal tube 210, which device 200 provides for improved control over the placement and direction of compressive forces on the interior of a patient's esophagus to compress the patient's aorta. More particularly, head assembly 240 of device 200 is configured for three, distinct degrees of freedom of movement, as best viewed in FIGS. 6 and 11. Specifically, clamp blades 241 move in the direction of arrow A toward and away from one another, which allow for easier entry of the distal end of device 200 into the patient's esophagus prior to separation of clamp blades 241 to push against the interior wall of the patient's esophagus. Further, the pitch of head assembly 240 with respect to esophageal tube 210 may be modified by rotating head assembly 240 in the direction of arrow B (in plane Bi of FIG. 11), and the yaw of head assembly 240 with respect to esophageal tube 210 may be modified by rotating head assembly in the direction of arrow C (in plane $C_1$ of FIG. 11), which additional movements provide for significantly improved control over the application of compressive force to the patient's esophagus and, in turn, the patient's aorta.

Figure 7:
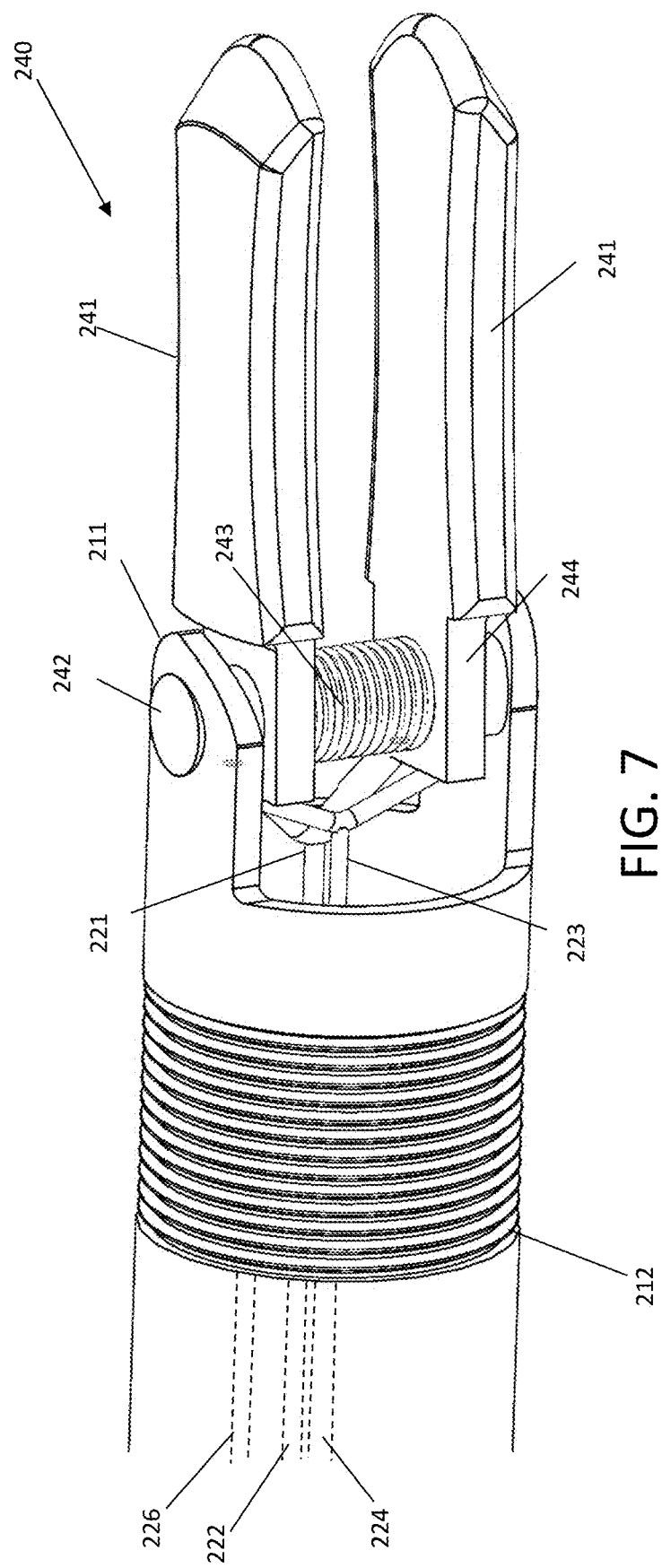
FIG. 7 is a close-up, top, partial sectional view of a head assembly of the device of FIG. 6.
Figure 8:
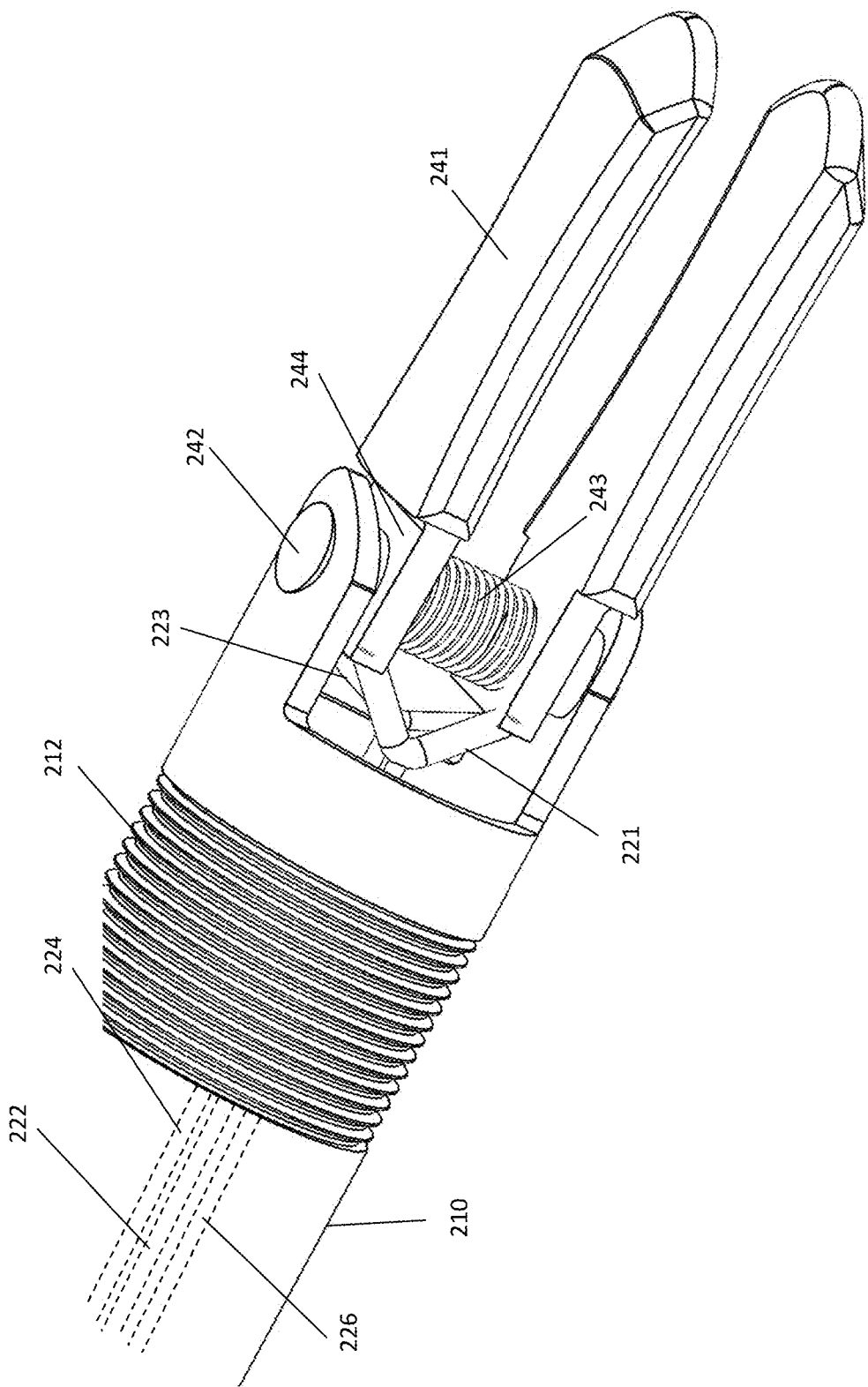
FIG. 8 is close-up, bottom perspective, partial sectional view of the head assembly of the device of FIG. 6.
Figure 9:
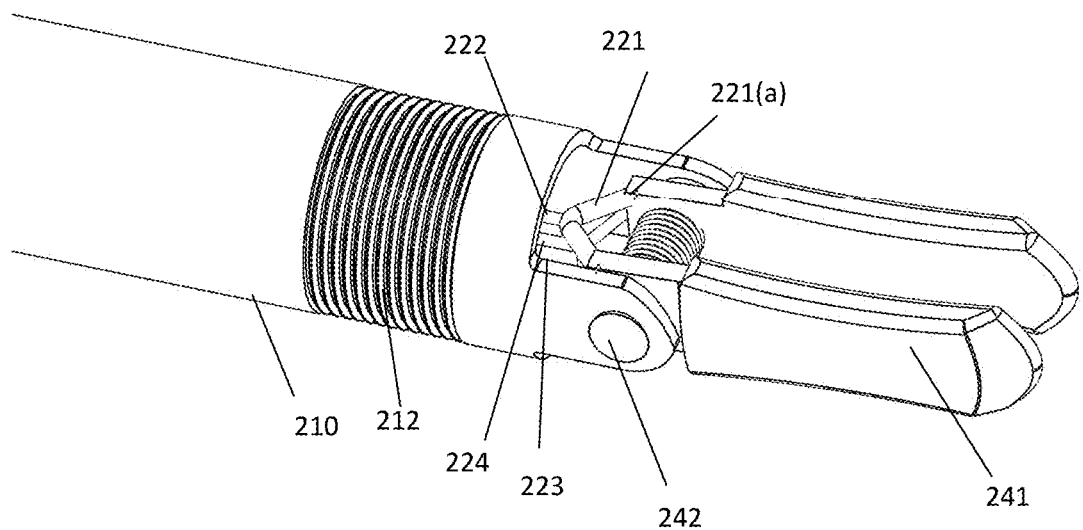
FIG. 9 is a close-up, side, partial sectional view of the head assembly of the device of FIG. 6.

With particular reference to FIGS. 7-9, head assembly 240 of device 200 includes clamp blades 241 that are slidably and pivotably mounted at mounting arms 244 to a pin 242, which pin 242 is mounted at distal end 211 of esophageal tube 210. Optionally, esophageal tube 210, or portions thereof, may extend distally past clamp blades 241, such that clamp blades 214 may extend through an opening in esophageal tube 210 when deployed to apply pressure to the patient's esophagus and aorta. A spring 243 is positioned between mounting arms 244 of clamp blades 241 and biases them away from one another and toward the interior walls of esophageal tube 210 at distal end 211. However, clamp blades 241 may also move toward one another to decrease a profile of head assembly 240 during insertion into a patient's esophagus. To effect such change in the distance between clamp blades 241, a clamp blade closing actuator 232 (FIG. 10) of actuator handle 220 is attached to clamp blade pitch control arms 244 through a clamp blade closure control connector cable 224 that extends through esophageal tube 210. As best viewed in FIGS. 7-9, clamp blade closure arms 223 are affixed at their distal ends to an outer face of clamp blade mounting arms 244, and at their proximal ends to clamp blade closure control connector cable 224, and are configured for scissor-like movement with respect to one another. Thus, as clamp blade closure control connector cable 224 is pulled via actuator 232 on actuator handle 220, clamp blade closure arms 223 come together, in turn pushing clamp blades 241 toward one another to decrease the profile of the distal end of device 200 as it is inserted into the patient's esophagus. Likewise, as clamp blade closure connector cable 224 is released, spring 243 biases clamp blades 241 away from one another for applying compressive pressure against the interior wall of the patient's esophagus.

Further, as clamp blades 241 are pivotably mounted to pin 242, clamp blades 241 may rotate about pin 242 to change the pitch of clamp blades 241 with respect to esophageal tube 210. To effect such change in pitch of clamp blades 241, a clamp blade pitch control actuator 231 (FIG. 10) of actuator handle 220 is attached to clamp blade pitch control arms 221 through a pitch control connector cable 222 that extends through esophageal tube 210. As shown in FIGS. 8 and 9, pitch control arms 221 are affixed to clamp blade mounting arms 244 at a location that is offset from a centerline of clamp blade mounting arms 244. Thus, as clamp blade pitch control connector cable 222 is pulled toward actuator handle 220, clamp blades 241 will pivot upward (from the perspective of FIG. 9) about pin 242, and as clamp blade pitch control connector cable 222 is pushed toward actuator handle 220, clamp blades 241 will pivot downward (from the perspective of FIG. 9). Thus, a physician may readily modify the pitch orientation of head assembly 240 with respect to esophageal tube 210 to a desired, optimal position so as to best apply pressure to the patient's esophagus at the desired location.

Figure 11:
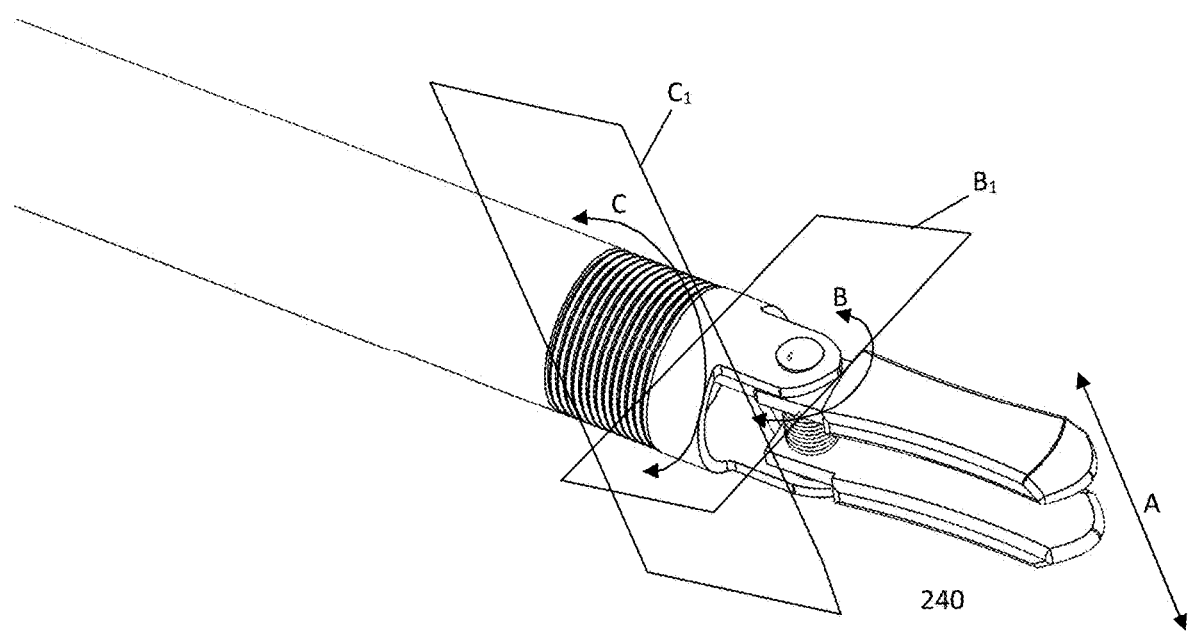
FIG. 11 is a top perspective, partial sectional view of the device of FIG. 6 showing three degrees of freedom of movement of the head assembly.
Figure 12:
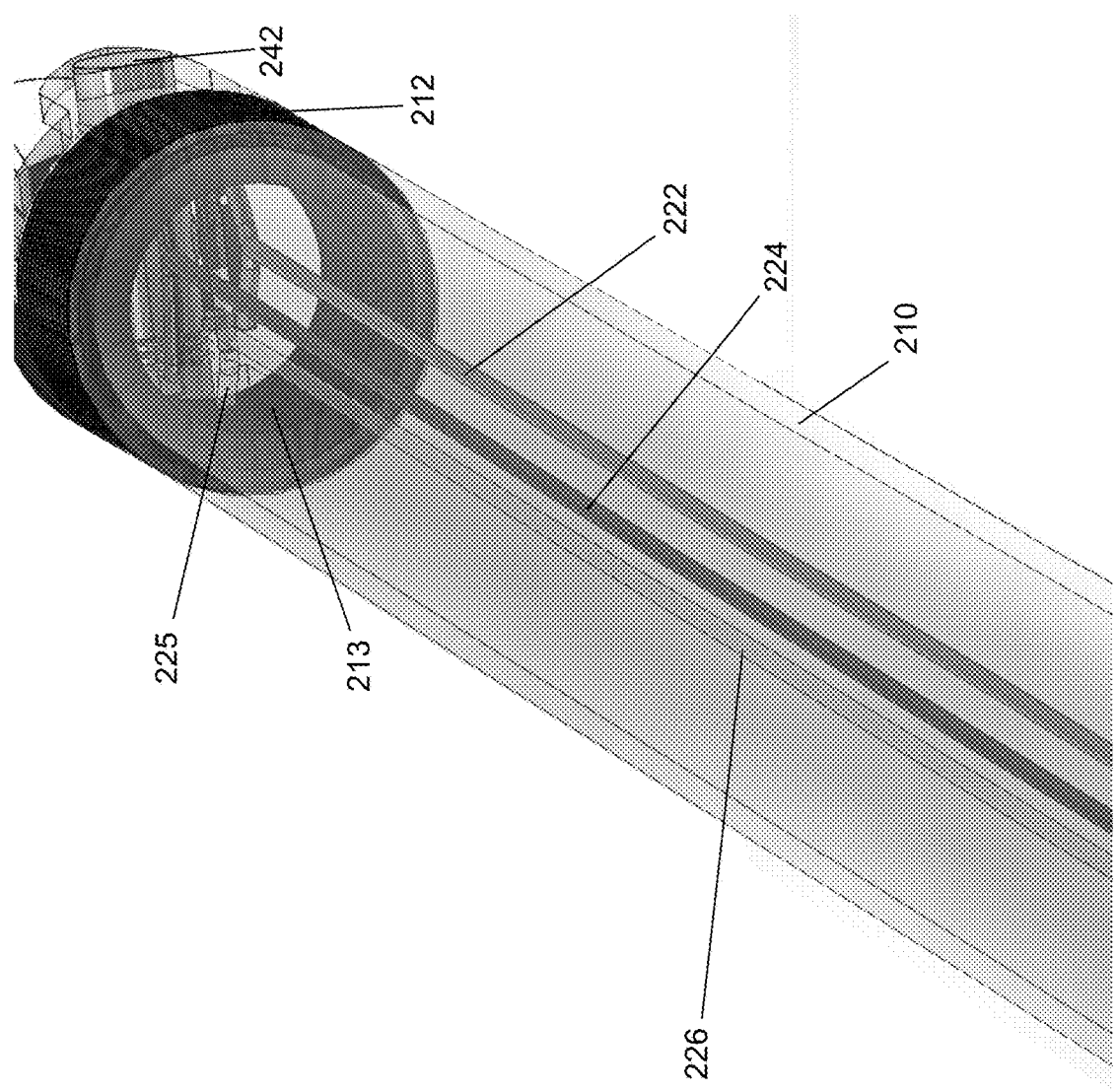
FIG. 12 is a top perspective, partial sectional view of the device of FIG. 6.

Still further, esophageal tube 210 preferably includes a flex section 212 that is positioned proximal to distal end 211 of esophageal tube 210. Flex section 212 is preferably formed of the same material as esophageal tube 210 (which may be of like configuration to a standard endoscope, by way of non-limiting example), but with an accordion-like structure that increases the flexibility of flex section 212 significantly beyond the flexibility of esophageal tube 210. Alternatively flex section 212 may be formed of an alternative, more highly flexible bio-compatible material as may occur to those of ordinary skill in the art. Flex section 212 is positioned so as to allow pivoting of head assembly 240 with respect to esophageal tube 210 in the direction of arrow C (FIGS. 6 and 11), thus modifying the yaw of such head assembly 240 to even further control the application of force from device 200 to the interior wall of the patient's esophagus and, in turn, to their aorta. To effect such change in yaw of head assembly 240, a clamp blade yaw control actuator 238 (FIG. 10) of actuator handle 220 is attached to the interior wall 213 of flex section 212 through a yaw control connector cable 226 that extends through esophageal tube 210. As shown in FIGS. 11 and 12, yaw control arms 225 are affixed to the interior wall 213 of flex section 212 so as to translate rotation of yaw control actuator 238 on handle 220 into pivoting of flex section 212. Thus, as clamp blade yaw control actuator 238 is rotated in a first direction, yaw control connector cable 226 pulls yaw control arms 225 in a first direction to pivot head assembly 240 in that first direction, and as clamp blade yaw control actuator 238 is rotated in a second, opposite direction, yaw control connector cable 226 pulls yaw control arms 225 in a second direction to pivot head assembly 240 in that second direction. Thus, a physician may likewise readily modify the yaw orientation of head assembly 240 with respect to esophageal tube 210 to a desired, optimal position so as to best apply pressure to the patient's esophagus at the desired location.

Figure 10:
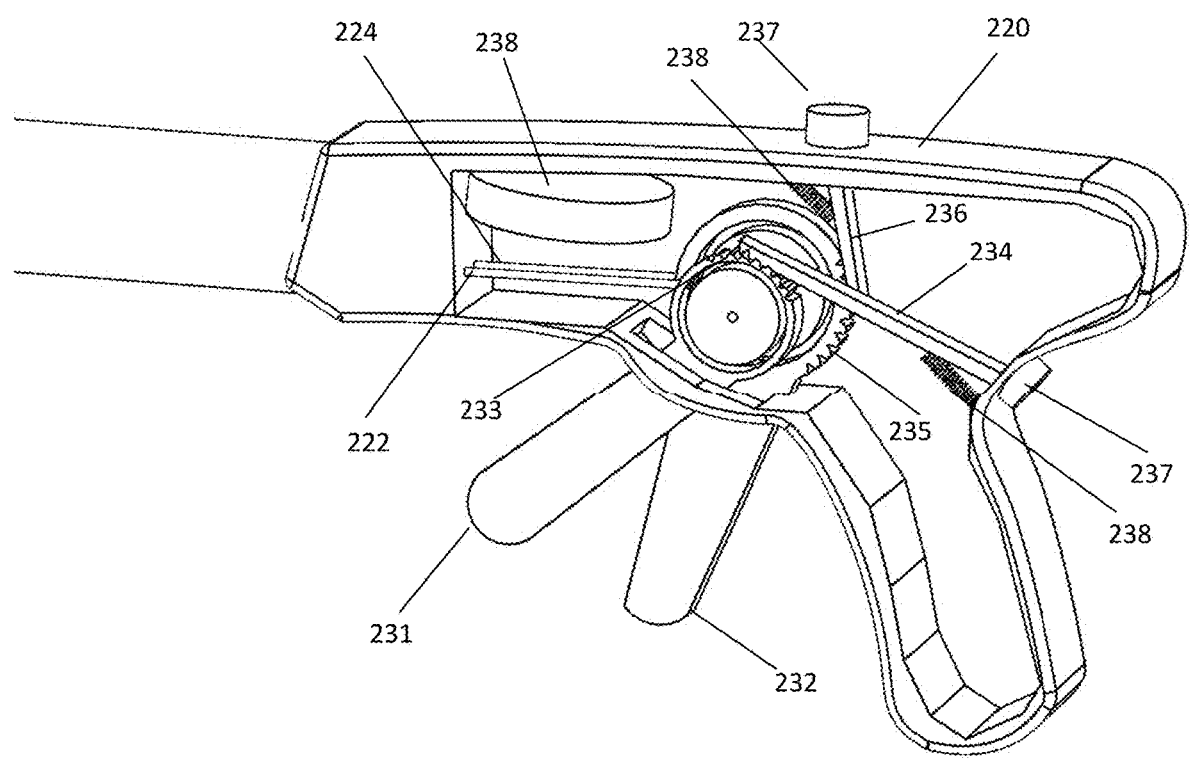
FIG. 10 is a close-up, side perspective sectional view of an actuator handle of the device of FIG. 6.

FIG. 10 provides a close-up view of the actuator mechanism of device 200 that allow a user to manipulate head assembly 240 through three distinct degrees of freedom of movement. Clamp blade pitch control actuator 231 is moveably mounted in actuator handle 220, and is attached to clamp blade pitch control connector cable 222. A head of pitch control actuator 231 is provided ratchet teeth 233 that releasably engage a pitch control actuator ratchet arm 234 that is biased by a spring 238 to engagement with teeth 233. Thus, as clamp blade pitch control actuator 231 is moved with respect to handle 220, its position with respect to handle 220 is locked by ratchet arm 234 to hold the position of pitch control actuator, and thus the pitch of head assembly 240, in place. A ratchet arm release 237 engages an end of pitch control actuator ratchet arm 234, which when engaged lifts ratchet arm 234 off of pitch control actuator ratchet teeth 233 to allow the physician to modify the pitch of head assembly 240. Similarly, clamp blade closing actuator 232 is moveably mounted in actuator handle 220, and is attached to clamp blade closure control connector cable 224. A head of closing actuator 232 is provided ratchet teeth 235 that releasably engage a closing actuator ratchet arm 236 that is biased by a spring 238 to engagement with teeth 235. Thus, as clamp blade closing actuator 232 is moved with respect to handle 220, its position with respect to handle 220 is locked by ratchet arm 236 to hold the position of clamp blade closing actuator 232, and thus the separation of clamp blades 241, in place. A ratchet arm release 237 similarly engages an end of closing actuator ratchet arm 236, which when engaged lifts ratchet arm 236 off of closing actuator ratchet teeth 235 to allow the physician to modify the separation between clamp blades 241. Finally, clamp blade yaw control actuator 238 is moveably mounted in actuator handle 220, and is attached to clamp blade yaw control connector cable 226, such that movement of clamp blade yaw control actuator 238 in either direction causes pivoting of head assembly 240 at flex section 212 of esophageal tube 210.

Optionally, one or more balloons, such as gastric balloon 10 of FIG. 3, may also be provided to even further control placement and direction of the application of compressive force against the interior of the patient's esophagus and, in turn, the patient's aorta. For example, a gastric balloon may be placed through esophageal tube 210 and extend out of distal end 211 of esophageal tube 210 and past clamp blades 241 for placement in the patient's stomach, thus aiding in proper positioning of head assembly 240 adjacent the desired portion of the patient's esophagus. Alternatively or additionally, a balloon may be positioned adjacent head assembly 240 which, when inflated, will push head assembly 240 in the desired direction toward the patient's aorta, thus both further anchoring the device 200 at the desired location in the patient's esophagus, and further isolating the direction of force application to the patient's esophagus.

Figure 13A:
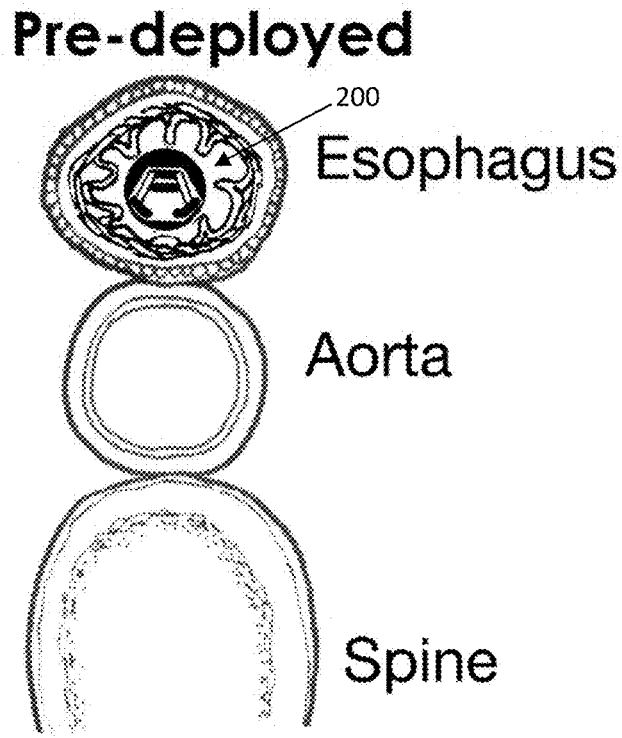
FIGS. 13(a) and 13(b) are cross-sectional views of a patient's esophagus, aorta and spine and showing deployment of a device in accordance with certain aspects of an embodiment.
Figure 13B:
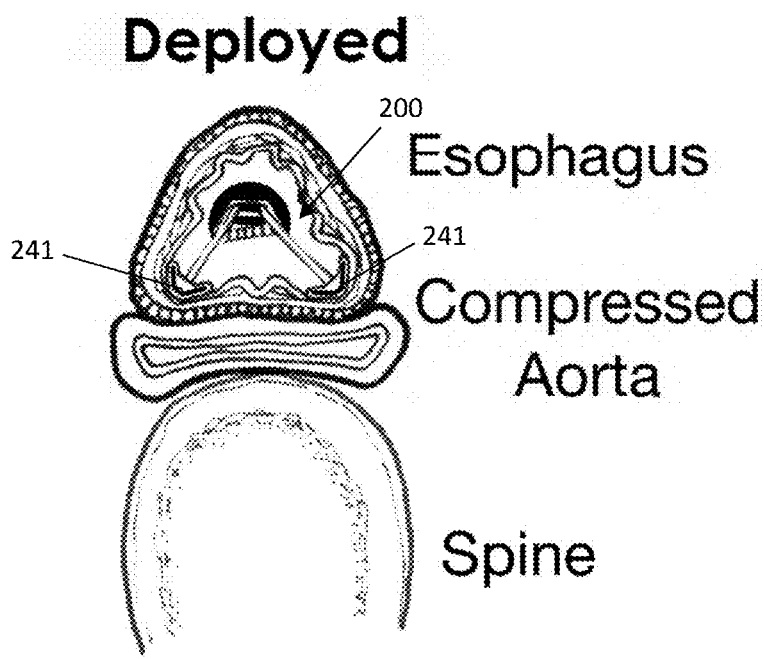

FIG. 13(a) provides a cross-sectional view of patient's esophagus, aorta, and spine, with device 200 positioned in the patient's esophagus at a location such that its deployment will cause impingement of the patient's aorta between their esophagus and spine, as shown in FIG. 13(b). As shown in FIGS. 13(a) and (b), in certain configurations, clamp blades 241 need not be parallel to one another. Rather, clamp blades 241 may be angularly offset from one another, such that as they pivot about pin 242, the distal ends of clamp blades 241 extend outward and away from one another, in turn expanding the width of esophageal tissue contacted by clamp blades 241, and in turn increasing the surface area of the patient's esophagus that applies an impinging force to the patient's aorta.

Figures 14A, 14B, 14C:
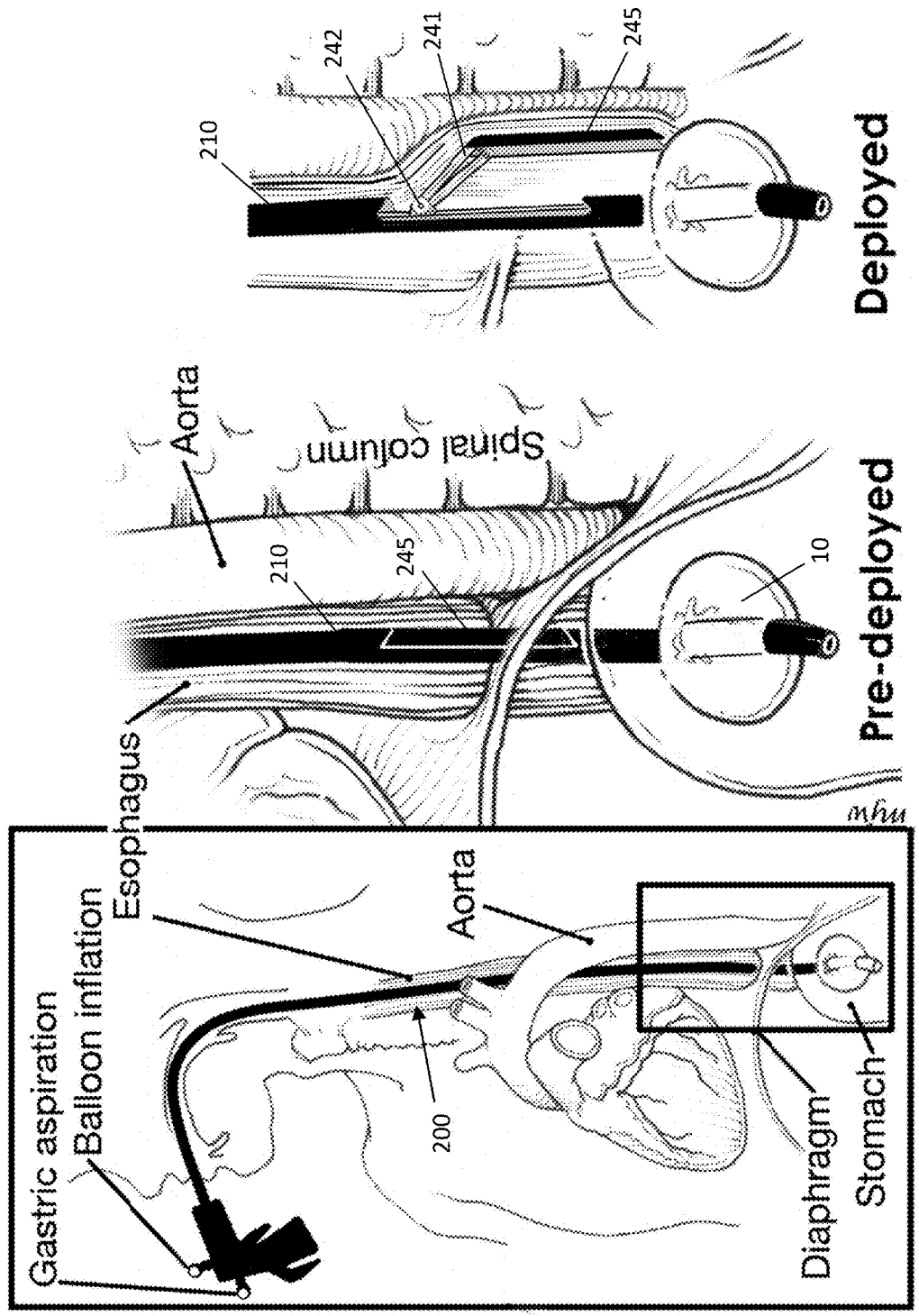
FIGS. 14(a), 14(b), and 14(c) are side views of a patient's esophagus, aorta and spine and showing deployment of a device in accordance with further aspects of an embodiment.

Further, FIGS. 14(a)-14(c) show views of a device 200 placed in a patient's esophagus, in which head assembly 240 of device 200 may include a plate 245 affixed to the distal ends of clamp blades 241. In certain configurations, plate 245 may form a portion of the outer wall of esophageal tube 210. In this configuration, as clamp blades 241 are rotated about pin 242, they lift plate 245 and push plate 245 against the interior wall of the patient's esophagus, such that plate 245 then compresses the patient's aorta by pushing against the esophageal wall. Optionally, separate plates 245 may be provided, with one such plate 245 attached to the distal end of each clamp blade 241. Such one or more plates 245 may be provided to increase the linear span of esophageal tissue contacted by device 200, and again in turn increase the surface area of the patient's esophagus that applies an impinging force to the patient's aorta.

Abdominal hemorrhage control presents a major unmet clinical need. By controlling the aortic flow in the descending portion of the aorta, methods and devices according to at least certain aspects of an embodiment substantially prevent blood flow to the lower chest and abdomen. This will significantly reduce blood loss and extend the life of the patient long enough to allow for a surgeon to access and repair the wound area. Methods and devices in accordance with certain aspects of an embodiment are configured to be less invasive and easier to implement for purposes of aortic occlusion than typical methods, such as REBOA. Methods and devices configured in accordance with at least certain aspects of the invention are further configured to be used in hospitals, emergency rooms, field operations, and trauma centers by many medical professionals, such as more than can use typical aortic occlusion methods.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. Thus, it should be understood, therefore, that the invention may be practiced otherwise than as specifically set forth herein.

REFERENCES

1. Arsenal Medical. "Foam System for Acute Hemorrhage." Arsenal Medical. 2017. http://www.arsenalmedical.com/foam-system-acute-hemorrhage.
2. Babin-Ebell, J., Gimpel-Henning, K., Sievers, H. H., & Scharfschwerdt, M. (2010). Influence of clamp duration and pressure on endothelial damage in aortic cross-clamping. Interactive cardiovascular and thoracic surgery, 10(2), 168-171.
3. Blikken, Wayland G. "Esophageal/Stethoscopic Gastric Tube." U.S. Patent and Trademark Office. U.S. Pat. No. 5,191,892. Mar. 9, 1993.
4. Compression Works. "Abdominal Aortic Junctional Tourniquet." Compression Works. http://compressionworks.com/products-aajt/.
5. Morrison, Jonathan J., and Todd E. Rasmussen. "Noncompressible torso hemorrhage: a review with contemporary definitions and management strategies." *Surgical Clinics of North America* 92.4 (2012): 843-858.
6. Riley, M. A., Walmsley, A. D., Speight, J. D., & Harris, I. R. (2002). *Magnets in medicine. Materials science and technology,* 18(1), 1-12.
7. Trauma Ready. "REBOA: Resuscitative Endovascular Balloon Occlusion of the Aorta." *Trauma Ready.* http://www.traumaready.com/reboa/kWjF8AEqnFPZ

What is claimed is:

1. A device for the esophageal compression of a patient's aorta, comprising:
an elongate tube;
an actuator handle at a proximal end of said elongate tube;
a head assembly at a distal end of said elongate tube wherein said head assembly comprises a pair of clamp blades that are spring biased away from one another and are mounted to said elongate tube for slidable movement along a first axis that is perpendicular to a second, longitudinal axis of said elongate tube, and are mounted to said elongate tube for pivotable movement about said first axis; and
an inflatable balloon adjacent the head assembly and configured to cause said balloon to be compressed between said head assembly and a patient's tissue when in an inflated state, wherein said balloon when inflated pushes said head assembly in a desired direction toward the patient's aorta;
wherein said actuator handle comprises a directional control mechanism configured to:
(i) pivot at least a portion of said head assembly about the first lateral axis;
(ii) pivot at least a portion of said head assembly about a second lateral axis that is perpendicular to said longitudinal axis and said first axis; and
(iii) expand a width of at least a portion of said head assembly to direct the application of pressure from said inflatable balloon to said patient's tissue.

2. The device of claim 1, wherein said pair of clamp blades comprise opposing contact surfaces configured to move away from one another when said balloon is inflated to increase a compression force against said patient's tissue.

3. The device of claim 1, said actuator handle further comprising a head assembly pitch control actuator moveably mounted to said handle and engaging said pair of clamp blades to pivot said clamp blades about said first axis, wherein pivoting of said clamp blades directs the compression force from said balloon.

4. The device of claim 1, said actuator handle further comprising a head assembly yaw control actuator movably mounted to said handle and engaging said head assembly to pivot said head assembly about said second lateral axis to adjust a position of said balloon compression.

5. The device of claim 4, said elongate tube further comprising a flex section of higher flexibility than a remainder of said elongate tube, wherein said flex section is positioned proximally from said distal end of said elongate tube to facilitate coordinated movement between said clamp blades and said balloon.

6. The device of claim 5, wherein said head assembly yaw control actuator engages said flex section to pivot said head assembly at said flex section while maintaining balloon compression against said patient's tissue.

7. A device for the esophageal compression of a patient's aorta, comprising:
an elongate esophageal tube having a longitudinal axis extending from a proximal end of said esophageal tube to a distal end of said esophageal tube;
an actuator handle at said proximal end of said esophageal tube;
a head assembly at said distal end of said esophageal tube, wherein said head assembly comprises a pair of clamp blades that are spring biased away from one another and are mounted to said esophageal tube for slidable movement along a first lateral axis that is perpendicular to said longitudinal axis, and are mounted to said esophageal tube for pivotable movement about said first lateral axis; and
an inflatable balloon adjacent the head assembly and configured to cause said balloon to be compressed between said head assembly and a patient's tissue when in an inflated state, wherein said balloon when inflated pushes said head assembly in a desired direction toward the patient's aorta;
wherein said actuator handle comprises a directional control mechanism configured to:
(i) pivot at least a portion of said head assembly about the first lateral axis;
(ii) pivot at least a portion of said head assembly about a second lateral axis that is perpendicular to said longitudinal axis and said first lateral axis; and
(iii) expand a width of at least a portion of said head assembly to direct the application of pressure from said inflatable balloon to said patient's tissue.

8. The device of claim 7, wherein said pair of clamp blades comprise opposing contact surfaces configured to move away from one another when said balloon is inflated to increase a compression force against said patient's tissue.

9. The device of claim 7, said actuator handle further comprising a head assembly pitch control actuator movably mounted to said handle and engaging said head assembly to pivot said head assembly about said first lateral axis.

10. The device of claim 7, said actuator handle further comprising a head assembly yaw control actuator movably mounted to said handle and engaging said head assembly to pivot said head assembly about said second lateral axis while maintaining balloon compression.

11. The device of claim 10, said esophageal tube further comprising a flex section of higher flexibility than a remainder of said esophageal tube, wherein said flex section is positioned proximally from a distal end of said esophageal tube.

12. The device of claim 11, wherein said head assembly yaw control actuator engages said flex section to pivot said head assembly at said flex section.

13. A method for applying impinging pressure to a patient's aorta from the patient's esophagus, comprising the steps of:
providing a device comprising:
an elongate esophageal tube having a longitudinal axis extending from a proximal end of said esophageal tube to a distal end of said esophageal tube;
an actuator handle at said proximal end of said esophageal tube;
a head assembly at said distal end of said esophageal tube, wherein said head assembly comprises a pair of clamp blades that are spring biased away from one another and are mounted to said esophageal tube for slidable movement along a first lateral axis that is perpendicular to said longitudinal axis, and are mounted to said esophageal tube for pivotable movement about said first lateral axis; and
an inflatable balloon adjacent the head assembly and configured to cause said balloon to be compressed between said head assembly and a patient's tissue when in an inflated state, wherein said balloon when inflated pushes said head assembly in a desired direction toward the patient's aorta;

wherein said actuator handle comprises a directional control mechanism configured to:
(i) pivot at least a portion of said head assembly about the first lateral axis;
(ii) pivot at least a second portion of said head assembly about a second lateral axis that is perpendicular to said longitudinal axis and said first lateral axis of said esophageal tube; and
(iii) expand a width of at least a portion of said head assembly to direct the application of pressure from said inflatable balloon to said patient's tissue;

positioning said device in said patient's esophagus so that said head assembly is positioned adjacent a crossing of said patient's esophagus over said patient's aorta;

inflating said balloon; and using said actuator handle to manipulate said head assembly to apply impinging pressure to the patient's aorta from the patient's esophagus.

14. The method of claim 13, wherein said step of using said actuator handle further comprises expanding the width of said head assembly to cause at least a portion of said head assembly to apply pressure against an interior wall of said patient's esophagus.

15. The method of claim 13, wherein said step of using said actuator handle further comprises pivoting said first portion of said head assembly about said first lateral axis to apply pressure against an interior wall of said patient's esophagus.

* * * * *